United States Patent
Gostein et al.

(10) Patent No.: US 9,564,853 B2
(45) Date of Patent: Feb. 7, 2017

(54) SOILING MEASUREMENT SYSTEM FOR PHOTOVOLTAIC ARRAYS

(71) Applicant: Atonometrics, Inc., Austin, TX (US)

(72) Inventors: Michael Gostein, Austin, TX (US); Stan Faullin, Austin, TX (US); Lawrence R. Dunn, Austin, TX (US); William Stueve, Austin, TX (US)

(73) Assignee: Atonometrics, Inc., Austin, TX (US)

( * ) Notice: Subject to any disclaimer, the term of this patent is extended or adjusted under 35 U.S.C. 154(b) by 0 days.

(21) Appl. No.: 14/381,165

(22) PCT Filed: Nov. 21, 2013

(86) PCT No.: PCT/US2013/071315
§ 371 (c)(1),
(2) Date: Aug. 26, 2014

(87) PCT Pub. No.: WO2014/081967
PCT Pub. Date: May 30, 2014

(65) Prior Publication Data
US 2015/0280644 A1    Oct. 1, 2015

Related U.S. Application Data

(60) Provisional application No. 61/728,898, filed on Nov. 21, 2012, provisional application No. 61/876,134, filed on Sep. 10, 2013.

(51) Int. Cl.
*G01N 21/00* (2006.01)
*H02S 50/15* (2014.01)
(Continued)

(52) U.S. Cl.
CPC .............. *H02S 50/15* (2014.12); *G01N 21/94* (2013.01); *G01R 29/24* (2013.01); *H02S 50/00* (2013.01)

(58) Field of Classification Search
CPC ......... H02S 50/00; G01R 29/24; G01N 21/94; F24J 2/407; A47K 5/00; B05B 11/00
See application file for complete search history.

(56) References Cited

U.S. PATENT DOCUMENTS 8,951,356 B2    2/2015   Fisher et al.
2002/0113084 A1*  8/2002  Gauthier .............. A47K 5/1217
                                                                222/65
(Continued)

FOREIGN PATENT DOCUMENTS

KR    10-0979848 B1    9/2010

OTHER PUBLICATIONS

R. Hammond, "Effects of Soiling on PV Module and Radiometer Performance", IEEE 1997.*

(Continued)

*Primary Examiner* — Kara E Geisel
*Assistant Examiner* — Maurice Smith

(57) ABSTRACT

A system for measuring the power or energy loss in a photovoltaic array due to soiling, which is the accumulation of dust, dirt, and/or other contaminants on the surfaces of photovoltaic modules, comprising: a pair of photovoltaic reference devices placed within or near the photovoltaic array and co-planar to the modules comprising the array, wherein one reference device is a module similar to those of the array and is allowed to accumulate soiling at the natural rate, and wherein the second reference device is a module or a cell and is periodically cleaned; and a measurement and control unit which measures and compares the electrical outputs of the soiled reference device and the clean reference device in order to determine the fraction of power lost by the soiled reference module due to soiling.

27 Claims, 10 Drawing Sheets

(51) Int. Cl.
*G01R 31/40* (2014.01)
*G01N 21/94* (2006.01)
*G01R 29/24* (2006.01)

(56) References Cited

U.S. PATENT DOCUMENTS

| | | | |
|---|---|---|---|
| 2005/0051209 A1* | 3/2005 | Choe | H02J 3/383 136/252 |
| 2008/0272279 A1* | 11/2008 | Thompson | H01L 31/02021 250/206 |
| 2009/0288691 A1* | 11/2009 | Hunt | B08B 3/02 134/57 R |
| 2010/0078058 A1* | 4/2010 | Nightingale | H01L 31/02021 136/244 |
| 2010/0320796 A1* | 12/2010 | Hoefer | B60R 13/07 296/93 |
| 2010/0332167 A1 | 12/2010 | Nuotio et al. | |
| 2011/0066401 A1* | 3/2011 | Yang | G01J 1/4228 702/184 |
| 2012/0037215 A1 | 2/2012 | Ball et al. | |

OTHER PUBLICATIONS

R Hammond, D. Srinivasan, A. Harris, K. Whitfield; Effects of Soiling on PV Module and Radiometer Performance; Photovoltaic Specialists Conference; Oct. 3, 1997; 1121-1124; 26th PVSC; Anaheim, CA; U.S.

A. Kimber, L. Mitchell, S. Nogradi, H. Wenger; The Effect of Soiling on Large Grid-Connected Photoboltaic Systems in California and the Southwest Region of the United States; Powerlight Comporation; 2391-2395; Berkeley, CA; U.S.

M. Garcia, L. Marroyo, E. Lorenzo, M. Perez; Soiling and other optical losses in solar-tracking PV plants in Navarra; Progress in Photovoltaics: Research and Applications; Jul. 15, 2010; 211-217; vol. 19, John Wiley & Sons, Ltd.

J. Riley Caron, B. Littmann; Direct Monitoring of Energy Lost Due to Soiling on First Solar Modules in California; IEEE Journal of Photovoltaics; Aug. 21, 2012; 1-5; IEEE.

* cited by examiner

| Condition | Description | Isc (A) | Pmax (W) | $SR_{Isc}$ | $SR_{Pmax}$ |
|---|---|---|---|---|---|
| A | Clean | 8.00 | 298.7 | 100.0% | 100.0% |
| B | Uniform Shading 10% on all cells | 7.20 | 267.7 | 90.0% | 89.6% |
| C | 10% Shading on 9 cells | 7.20 | 285.9 | 90.0% | 95.7% |
| D | 10% Shading on 1 cell | 8.00 | 290.5 | 100.0% | 97.2% |

FIGURE 4
FIGURE 4A
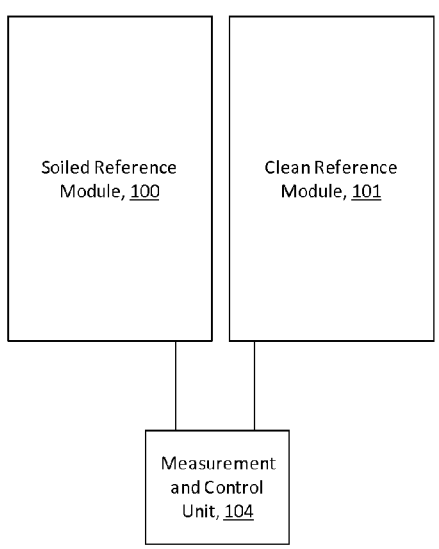
FIGURE 4B
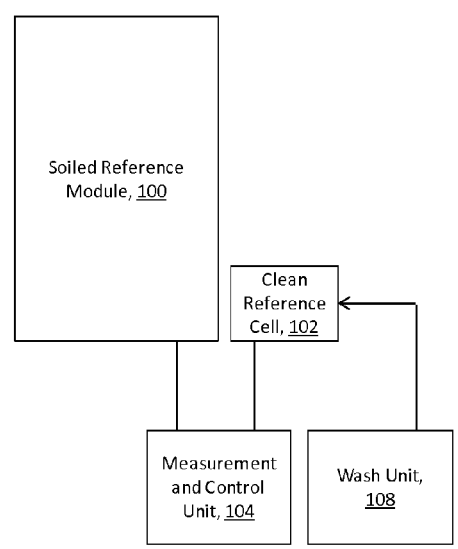

SOILING MEASUREMENT SYSTEM FOR PHOTOVOLTAIC ARRAYS

CROSS-REFERENCE TO RELATED APPLICATIONS

The present application claims priority to U.S. Provisional Patent Application Ser. No. 61/876,134, filed Sep. 10, 2013; and PCT Patent Application Ser. No. PCT/US13/71315, which are incorporated herein by reference.

FIELD OF THE INVENTION

The invention relates to a system for measuring power or energy loss in solar power plants due to accumulation of dust, dirt, and other contaminants (or "soiling") on photovoltaic (PV) modules.

BACKGROUND OF THE INVENTION

Arrays of photovoltaic (PV) modules, also known as solar panels, are used in solar power installations for converting sunlight to electricity. Such installations range from small rooftop systems on residential or commercial buildings to large utility-scale facilities including thousands or millions of PV modules. Collectively, we refer to these as "solar power plants."

Frequently solar power plants employ performance monitoring systems, especially in large commercial or utility-scale facilities. These systems monitor output power and meteorological conditions, allowing plant developers and owners to confirm that performance meets expectations and allowing system operators to identify fault conditions or underperforming equipment.

Among the most significant meteorological conditions affecting solar power plant performance are the solar irradiance at the site, the ambient temperature at the site, and the accumulation of dust and dirt or other contaminants on the PV modules.

Accumulation of dust, dirt, or other contaminants is known as "soiling". Soiling reduces the solar irradiance transmitted to the active area of the PV modules, thus reducing power output. Soiling levels of PV modules accumulate in between rainfalls or scheduled cleanings of the PV array. Losses often accumulate at rates of approximately 0.1% to 0.3% additional power loss per day, depending on local conditions at the site, and may accumulate up to levels of ~5-20% power loss (or greater) during extended periods without rainfall.

Developers, owners, and operators of solar power plants wish to quantify power losses due to soiling in order to confirm the underlying performance of the power plant and also to determine if and when cleaning the PV array provides an economic payback.

In addition, prior to construction of a solar power plant, developers, owners, and operators often wish to assess conditions at a site for a prospective solar power plant, in order to determine how site conditions—including soiling—may affect the performance of the prospective solar power plant.

Losses due to soiling may be quantified for an operating solar power plant by monitoring the overall efficiency of the solar power plant versus expectations based on meteorological conditions, for example as discussed in Kimber, et al, "The Effect of Soiling on Large Grid-Connected Photovoltaic Systems in California and the Southwest Region of the United States," *Conference Record of the* 2006 *IEEE 4th World Conference on Photovoltaic Energy Conversion*, vol. 2, pp. 2391-2395, May 2006. However, this method assumes that all efficiency losses are due to environmental factors and that there is no underlying fault or degradation in the solar power plant performance that would also result in efficiency loss. This method also does not apply to assessing soiling-related power losses from prospective solar power plants prior to construction.

Another method quantifies soiling-related losses by comparing the temperature-corrected short-circuit current of two identical test modules representative of those in the PV array, one of which (the "soiled" module) is allowed to soil at the natural rate of the PV array and the other of which (the "clean" module) is kept clean, through either manual or automatic washing. This method utilizes the principles that the temperature-corrected short-circuit current of a PV module is proportional to the irradiance reaching the module, and that the power produced is a known function of irradiance. The short-circuit current is typically measured by means of the voltage drop across a very low-resistance shunt resistor connected between the module terminals. This method is described, for example, by R. Hammond, et al, "Effects of Soiling on PV Module and Radiometer Performance," *Proceedings of* $26^{th}$ *IEEE Photovoltaics Specialist Conference (PVSC)*, Anaheim, Calif., September 30-Oct. 3, 1997; Miguel Garcia, et al, "Soiling and Other Optical Losses in Solar-Tracking PV Plants in Navarra," *Progress in Photovoltaics: Research And Applications*, vol. 19, pp. 211-217, 2011; Caron, et al, "Direct Monitoring of Energy Lost Due to Soiling on First Solar Modules in California," *Proceedings of the* $38^{th}$ *IEEE Photovoltaic Specialists Conference (PVSC)*, Austin, Tex., Jun. 3-8, 2012; and Caron, et al, "Direct Monitoring of Energy Lost Due to Soiling on First Solar Modules in California," *IEEE Journal of Photovoltaics*, vol. PP, no. 99, pp. 1-5, Oct. 24, 2012.

However, since this method estimates power loss from measurements of short-circuit current, i.e. from effective irradiance reaching the module, it will yield inaccurate results in certain situations, principally when the soiling is accumulated non-uniformly across the surfaces of the modules. Such non-uniform distributions of soiling frequently occur due to the influences of module orientation, wind, rain, and gravity, often resulting in predominant soiling across one edge or another localized region of the modules, as illustrated in photographs of soiled photovoltaic arrays shown in FIG. 1A and FIG. 1B. Various distributions of soiling can lead to different ratios between the modules' short-circuit current and output power at a given irradiance. This is explained in more detail below.

Furthermore, the method described above requires keeping one of the two identical PV modules clean, with cleaning preferably performed daily. The cleaning can be performed manually, although this creates significant labor expenses. Alternatively, an automated system can be used to keep the clean module washed. However, this may require significant water usage. As water supplies are not typically available at solar power plant installations, especially in remote or desert sites, large storage tanks may be required to operate such equipment. This is expensive and creates maintenance problems.

BRIEF SUMMARY OF THE INVENTION

The disclosed subject matter provides a system for measuring the fraction of power or energy lost due to PV module soiling in an actual solar power plant or a prospective solar power plant to be constructed at or near the site of the measuring system. The disclosed subject matter addresses the shortcomings of existing technology and practices by providing more accurate measurements and more economical apparatus with minimized maintenance requirements.

The system comprises a soiled reference module 100 and a clean reference device which may be either a clean reference module 101 or a clean reference cell 102. The pair of reference devices (100 and 101, or 100 and 102) are coupled to a measurement and control unit 104 and are mounted on a mounting rack 106, substantially co-planar with each other and substantially co-planar with the modules of the actual or prospective solar power plant. The system is placed outdoors at the site of the actual or prospective solar power plant, and, in the case of an actual solar power plant, is located substantially near or within the photovoltaic array 10 of the solar power plant as depicted in FIG. 2.

The soiled reference module 100 is of substantially the same type and is mounted in substantially the same way as the PV array 10 modules used in the actual or prospective solar power plant, and is therefore allowed to accumulate soiling in the same manner and at the same rate.

In one embodiment, the clean reference device is a clean reference cell 102, which is relatively small compared to a full-size module.

In one embodiment, the clean reference device (101 or 102) is periodically cleaned with an automated system, which may include high-pressure spraying with a cleaning fluid 306, cleaning with mechanical action, cleaning with a pressurized gas flow, or combinations thereof. In one embodiment, the system, apparatus or method includes a collection tray, capable of capturing the dispensed cleaning fluid for re-use.

The measurement and control unit 104 measures the soiled reference module 100 temperature and electrical output parameters, including both the short-circuit current and maximum power, as well as the solar irradiance detected by the clean reference cell 102 (or clean reference module 101). These quantities are analyzed, either by the measurement and control unit 104 or by a remote computing system (not shown) in order to determine the expected electrical output power of the soiled reference module 100 at the given conditions of temperature and irradiance in the absence of soiling, and there from to determine the fraction of output power from the soiled reference module 100 that is lost due to soiling, or, equivalently, the fraction of power actually generated in the soiled state compared to the power which could be generated in the absence of soiling.

Particular objects of the disclosed subject matter include: measuring the soiling-related power loss and/or the rate-of-change of soiling-related power loss over time; measuring such losses accurately for modules of the same type used in the actual or prospective solar power plant; measuring such losses accurately for both uniform and non-uniform distribution of soiling across a module; and providing an economical, automated measuring system requiring minimal maintenance. Any particular embodiment does not necessarily contain all the preceding objects, and one or more of the preceding objects may be added or removed from an embodiment and stay within the scope of this disclosure.

A system according to the disclosed subject matter achieves the aforementioned objects through the following major aspects which together improve upon existing technology and practices: the soiled reference module 100 is substantially identical to those in the PV array 10 and mounted in substantially the same manner, therefore accumulating soiling-related power losses in a manner representative of the PV array 10; both the short-circuit current and maximum power output of the soiled reference module 100 can be measured, accounting for the effects of possible non-uniform soiling; measurements of the soiled reference module 100 are analyzed together with measurements from a clean reference device (101 or 102) allowing discrimination of soiling-induced losses from other losses; in one embodiment a relatively small clean reference cell 102 is used as the clean reference device, and, in one embodiment, the clean reference cell 102 is cleaned with an automated system, which requires minimal cleaning fluid usage due to the relatively small size of the clean reference cell 102.

In one embodiment, the reference devices (100, 101, and/or 102) can be maintained in a defined state in between measurements, thus maximizing their expected life span. Examples of this state include: short-circuit state, an open-circuit state, and a maximum power state.

In one embodiment, the system calculates and measures a current-voltage relationship from which are determined the short-circuit current, an open-circuit voltage, and/or a maximum power output.

One embodiment of the present disclosure includes a system, apparatus and method for determining and responding to non-uniform soiling of system, apparatus or photovoltaic array.

One embodiment of the present disclosure includes a system, apparatus and method for responding to a difference in angular alignment between that of the clean and soiled reference devices, and/or the apparatus and the photovoltaic array.

These and other aspects of the disclosed subject matter, as well as additional novel features, will be apparent from the description provided herein. The intent of this summary is not to be a comprehensive description of the subject matter, but rather to provide an overview of some of the subject matter's functionality. Other systems, methods, features and advantages here provided will become apparent to one with skill in the art upon examination of the following FIGURES and detailed description. It is intended that all such additional systems, methods, features and advantages that are included within this description be within the scope of the accompanying claims.

BRIEF DESCRIPTION OF THE DRAWINGS

The novel features believed characteristic of the disclosed subject matter will be set forth in the claims. The disclosed subject matter itself, however, as well as a preferred mode of use, further objectives, and advantages thereof, will best be understood by reference to the following detailed description of illustrative embodiments when read in conjunction with the accompanying drawings, wherein:

FIG. 4 depicts alternate embodiments of the disclosed subject matter, wherein soiling is determined from soiled reference module 100 and wherein solar irradiance for reference in soiling determination is measured with either A) a clean reference module 101, substantially identical to soiled reference module 100, and which is cleaned either manually or automatically or B) a clean reference cell 102 which may be automatically cleaned by wash unit 108 of the disclosed subject matter.

In the figures, like elements should be understood to represent like elements, even though reference labels may be omitted on some instances of a repeated element for simplicity.

DETAILED DESCRIPTION OF ILLUSTRATIVE EMBODIMENTS

The disclosed subject matter provides a system for measuring the fraction of power lost due to PV module soiling in an actual solar power plant or a prospective solar power plant to be constructed at or near the site of the measuring system.

Although described with particular reference to a soiling measurement system for solar power plants, those with skill in the arts will recognize that the disclosed embodiments have relevance to a wide variety of areas in addition to those specific examples described below.

All references, including publications, patent applications, and patents, cited herein are hereby incorporated by reference to the same extent as if each reference were individually and specifically indicated to be incorporated by reference and were set forth in its entirety herein. Provided, however, to the extent there exists a conflict between this disclosure and anything incorporated by reference, this disclosure shall supersede.

Non-Uniform Soiling

PV array modules undergo soiling as dust, dirt, or other contaminants accumulate on them. Under many conditions, soiling accumulates uniformly across the surfaces of the modules. However, under other conditions, soiling may accumulate non-uniformly on the modules. In many solar power plants, modules are installed at a tilt angle to better face the sun. In this case a condition leading to non-uniform soiling commonly occurs when water condensation on the modules rinses dust and dirt from the tops towards the bottoms of the modules, without completely cleaning them. This leaves a band of soiling accumulation across the bottoms of the modules—referred to as "edge soiling". The extent of the edge soiling effect may depend on framing, tilt angle, and mounting mechanisms of the module, as these affect the pattern of water flow across the module surface. Other conditions may also lead to non-uniform soiling of various patterns, such conditions including wind effects; specific details of the module construction and/or mounting system; behavior of a tracking system which adjusts module orientation, if used; and/or other details of the site.

Figure 1A:
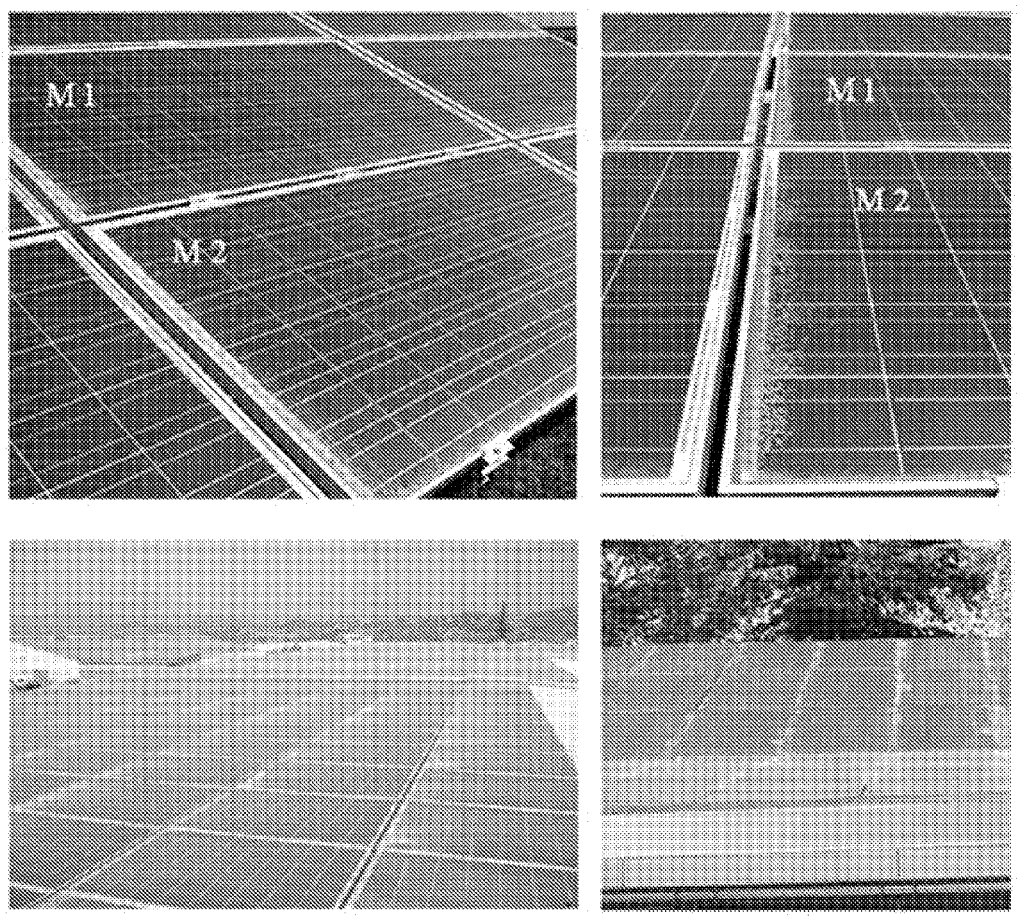
FIG. 1 illustrates soiling accumulation on photovoltaic arrays, with examples that particularly demonstrate spatially non-uniform soiling accumulation. The photograph in FIG. 1A is extracted from E. Lorenzo, R. Moreton, and I. Luque, "Dust effects on PV array performance: in-field observations with non-uniform patterns," *Progress in Photovoltaics: Research and Applications*, 2013, which is incorporated herein by reference, wherein i) illustrates a soiled PV array in a solar park, ii) is a detail of i), and iii) and iv) illustrate soiled rooftop photovoltaic arrays.
FIG. 1B is extracted from F. Brill, "EnviroPolitics Blog: PSEG building solar farms—and not just in New Jersey," 16 Nov. 2012, (Online), Available: http://enviropoliticsblog.blogspot.com/2012/11/pseg-building-solar-farms-and-not-just.html#.UagS95xXqdI (Accessed: 31 May 2013), which is incorporated herein by reference, and depicts a soiled PV array with modules mounted on a one-axis tracking system and spatially non-uniform accumulation of soiling.
Figure 1B:
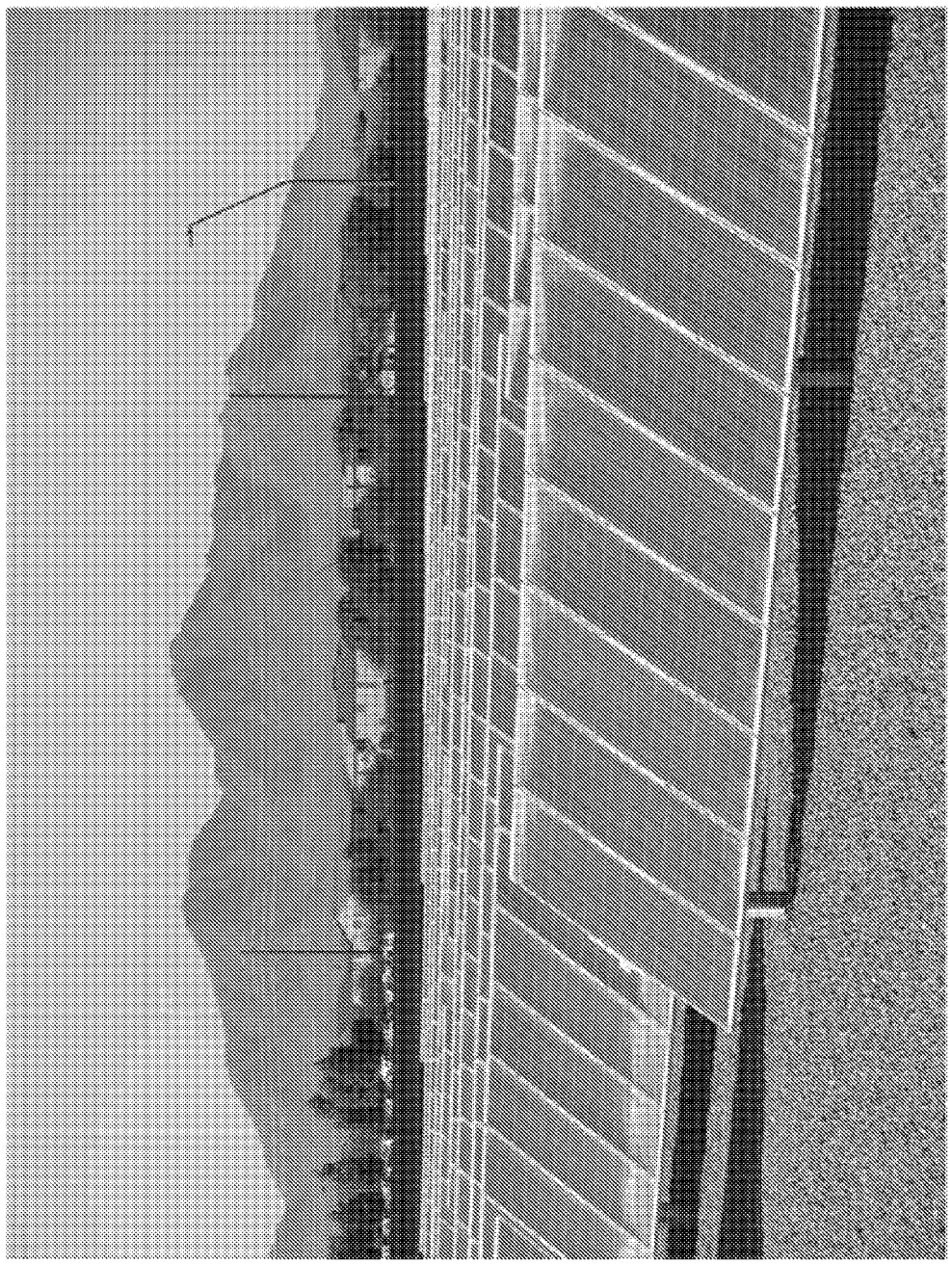
Figure 2:
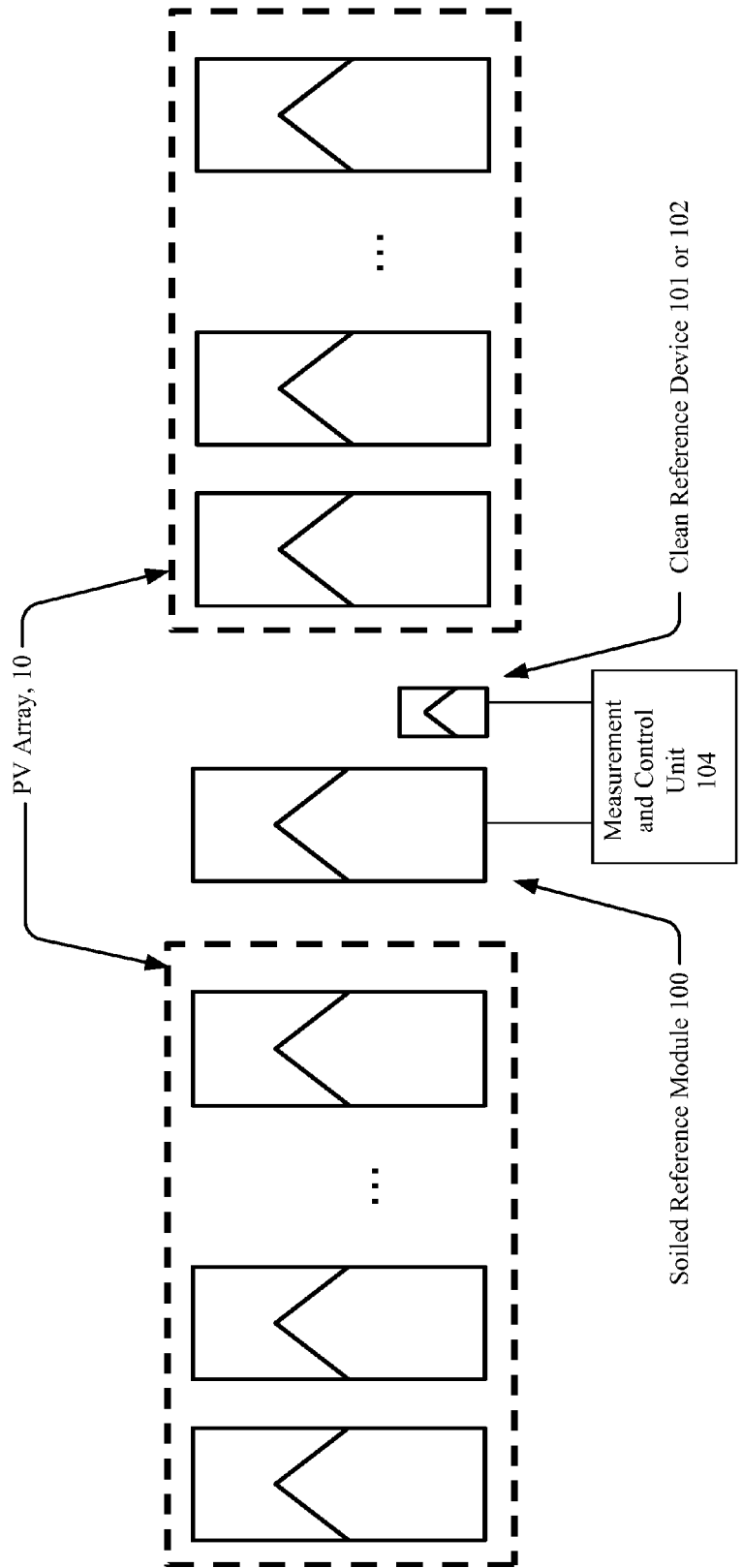
FIG. 2 depicts a soiling measurement system according to the disclosed subject matter, located substantially near or within a photovoltaic array to be monitored.
Figure 3:
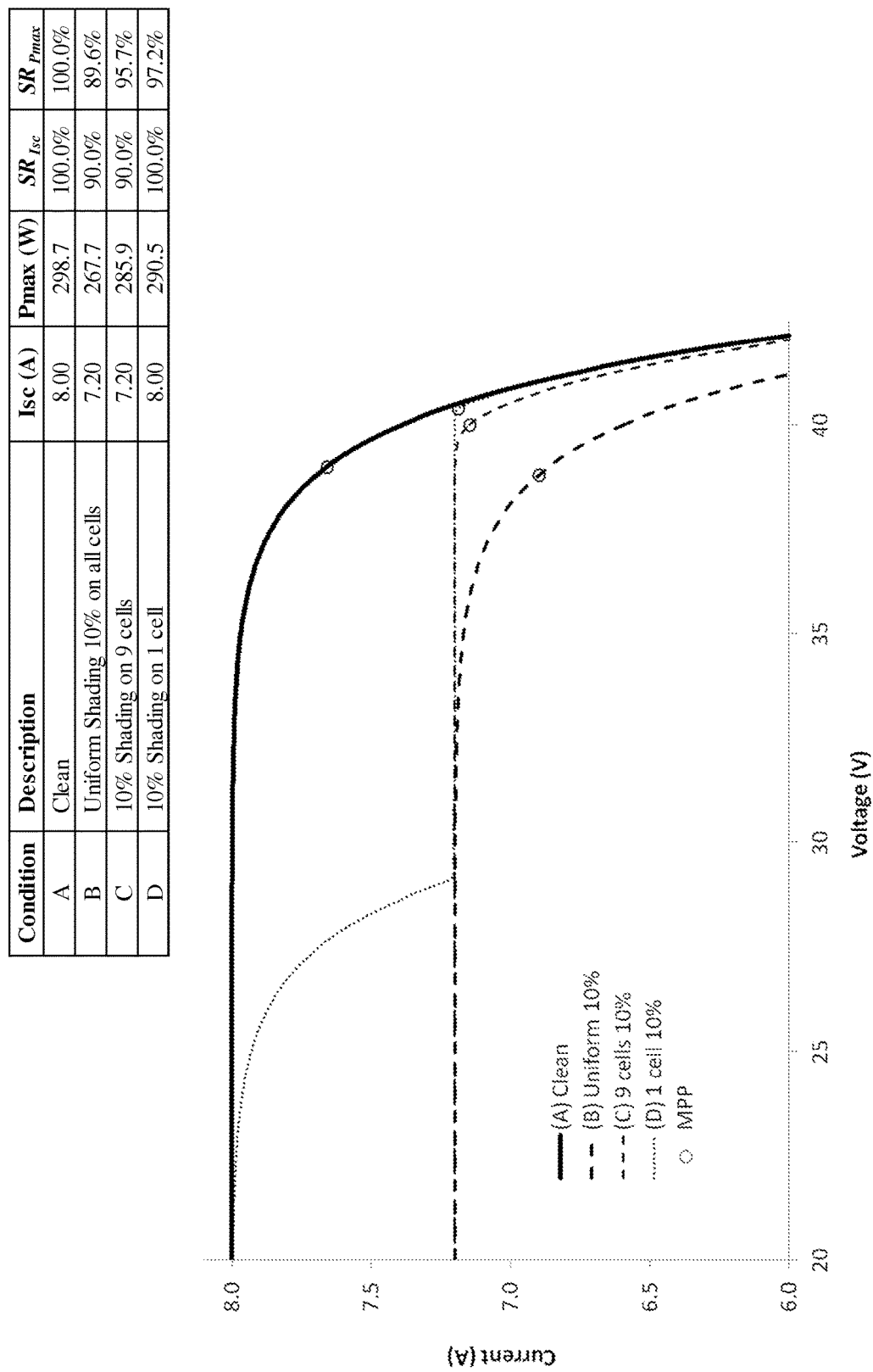
FIG. 3 depicts the effects of uniform and non-uniform soiling on the short-circuit current and maximum power of a PV module, using simulated I-V curves of a 72-cell PV module under various conditions. Open circles represent the maximum power point of each curve.

Uniform and non-uniform soiling have different effects on the electrical output characteristics of PV modules. This is illustrated in FIG. 3, which depicts simulated I-V curves of a hypothetical 72-cell, –300 W PV module under various conditions. Simulated I-V curves were generated with a commercial circuit modeling software package, according to techniques familiar to those skilled in the art. The module is taken to have all 72 cells connected in series, with no bypass diodes. Condition A represents the clean state of the module, while conditions B, C, and D represent various soiled states, with different shading resulting from the pattern of soiling. FIG. 3 shows the simulated I-V curve for each condition, as well as the short-circuit current ($I_{sc}$) and maximum power ($P_{max}$) value corresponding to each curve. The maximum power point of each curve is also indicated with an open circle. The reduction in either $I_{sc}$ or $P_{max}$ due to soiling is quantified by a soiling ratio (SR), calculated as the ratio of the $I_{sc}$ r $P_{max}$ value measured in the soiled state to that measured in the clean state. These values are denoted $SR_{Isc}$ and $SR_{Pmax}$, respectively on the FIGURE. In the present case we assume the module to be at the same temperature in the clean and soiled state, and therefore neglect temperature normalization of the quantities, which should be considered in the general case.

Condition B corresponds to uniform soiling leading to an equal 10% shading of all cells. In this case, $I_{sc}$ and $P_{max}$ are reduced to 90% and 89.6% of their values for the clean state, respectively, and $1-SR_{Isc}$ is a good approximation of the portion of power lost due to soiling.

Condition C corresponds to a 10% shading of 9 of the cells, and is intended to represent an edge soiling condition, while condition D corresponds to a 10% shading of 1 cell, representing a localized contaminant on part of the module. Note that in condition D, the I-V curve shows a step between approximately 25 V and 28 V on the x-axis arising from the reverse biasing of the one shaded cell by the remaining non-shaded cells at voltages less than about 25 V.

It is apparent from the tabulated values in FIG. 3 that the non-uniform soiling conditions exhibit different reductions in $I_{sc}$ versus $P_{max}$ as compared with the clean state. In particular, conditions B and C, corresponding to uniform soiling and edge soiling, respectively, cannot be distinguished on the basis of changes in the $I_{sc}$ values, even though the effects on $P_{max}$ values are very different. Accordingly, $1-SR_{Pmax}$ is a much better metric of power lost due to soiling as compared with $1-SR_{Isc}$.

The conditions illustrated in FIG. 3 are only representative examples. Details of module construction, including number and arrangement of cells and any included bypass diodes, lead to different kinds of behavior under various patterns of soiling. In general, for spatially uniform soiling, the soiling-induced reductions in $I_{sc}$ and $P_{max}$ are similar, while for sufficiently non-uniform soiling they are not. This illustrates the benefit of measuring $P_{max}$ values as a central aspect of a system according to the disclosed subject matter.

System Overview

FIG. 4 depicts two embodiments of the disclosed subject matter. In both embodiments, soiling is determined from measurements performed by the measurement and control unit 104 of the $I_{sc}$ and $P_{max}$ of soiled reference module 100, which is substantially identical to modules comprising the PV array of the solar power plant and which is mounted in substantially identical manner. The measured $I_{sc}$ and $P_{max}$ must be normalized to account for both the soiled reference module 100 temperature and the incident solar irradiance. In one embodiment, depicted in FIG. 4A, solar irradiance is measured using a clean reference module 101 substantially identical to the soiled reference module 100. The clean reference module 101 is cleaned either manually or by an automatic system. In another embodiment, depicted in FIG. 4B, solar irradiance is measured using a clean reference cell 102, which is relatively small compared to clean reference module 101 and which, in one embodiment, is automatically cleaned by wash unit 108 of the disclosed subject matter.

Figure 5:
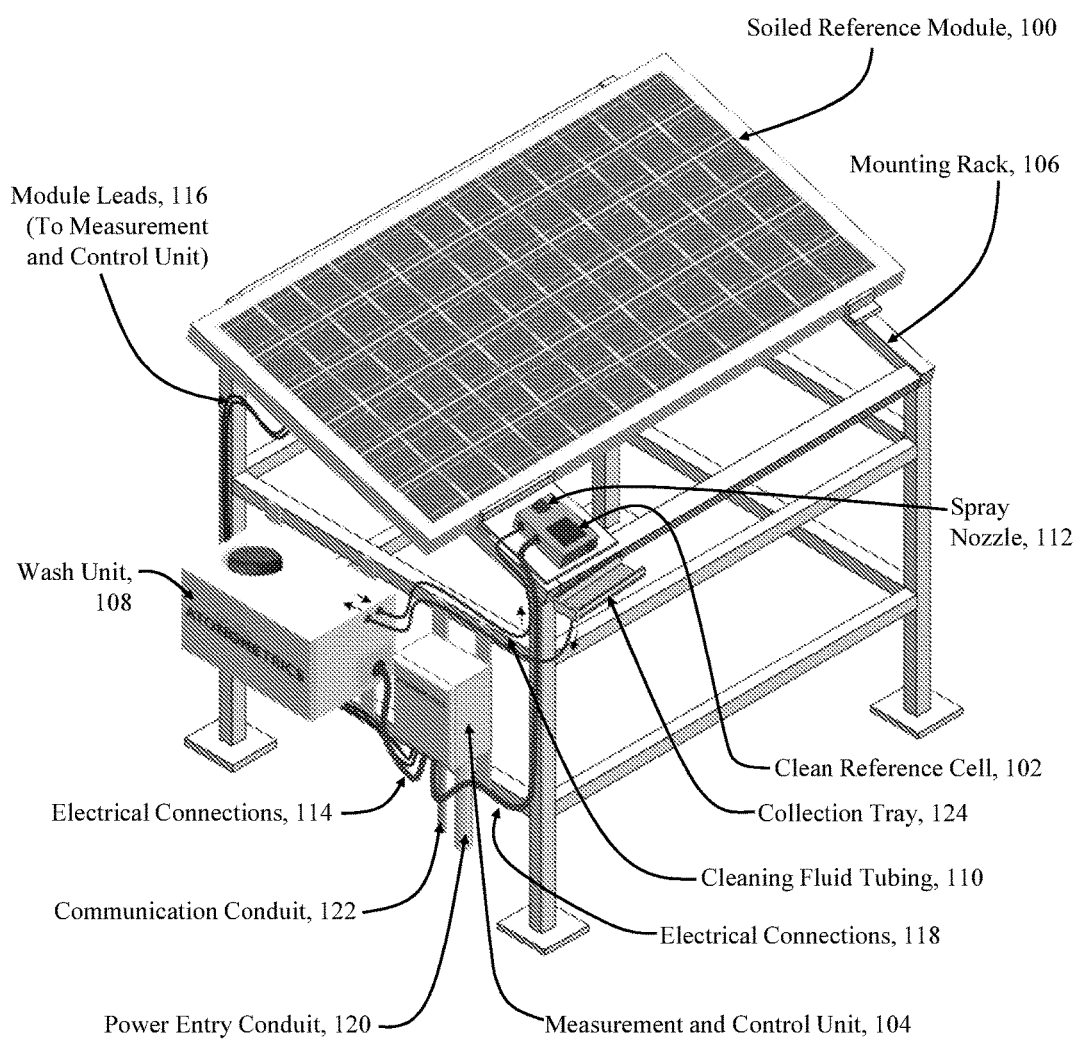
FIG. 5 depicts one embodiment of a system according to the disclosed subject matter.

FIG. 5 depicts an embodiment of the type disclosed in FIG. 4B, which is now discussed in greater detail.

In FIG. 5, the system comprises a soiled reference module 100 and a clean reference cell 102 coupled to a measurement and control unit 104, which are placed outdoors at the site of the actual or prospective solar power plant.

The soiled reference module 100 and clean reference cell 102 are mounted on a mounting rack 106, substantially co-planar with each other and substantially co-planar with the modules of the actual or prospective solar power plant.

The clean reference cell 102 is periodically cleaned with an automated system, which may include spraying with a cleaning fluid and/or cleaning with mechanical action. In a representative embodiment, cleaning is performed once per day. In one embodiment, a wash unit 108, comprising a fluid reservoir and a pump, delivers cleaning fluid through cleaning fluid tubing 110 to a spray nozzle 112 housed within or above the reference cell 102 enclosure, such that the cleaning fluid removes accumulated soiling from the clean reference cell 102. The wash unit 108 is controlled by the measurement and control unit 104 via electrical connections 114. In another embodiment, the system includes a mechanical device (not shown), such as a wiper blade, which removes accumulated soiling from the clean reference cell 102 either with or without the aid of cleaning fluid.

The soiled reference module 100 is of substantially the same type and is mounted in substantially the same way as the modules used in the actual or prospective solar power plant, and is therefore allowed to accumulate soiling in the same manner and at the same rate. Soiling-related losses in the output power of the soiled reference module 100 are therefore deemed representative of soiling-related power losses in the solar power plant.

The soiled reference module 100 is electrically connected to the measurement and control unit 104 via its module leads 116. In one embodiment, a temperature sensor (not shown), such as a Resistance Temperature Device (RTD), is attached to the back side of the soiled reference module 100 and connected to the measurement and control unit 104 in order to provide for measuring the soiled reference module 100 temperature.

The clean reference cell 102 is used to provide an independent measure of solar irradiance. It is electrically connected to the measurement and control unit 104 via electrical connections 118 which also include signals from a temperature measurement device, such as an RTD, in thermal contact with the PV-active portion of the clean reference cell 102. In one embodiment, an optical filter is integrated within the clean reference cell 102 in order to reduce its spectral response mismatch versus that of the soiled reference module 100; this is of particular benefit when the underlying PV technologies of the clean reference cell 102 and soiled reference module 100 are different.

The measurement and control unit 104 measures the electrical output parameters and temperature of the soiled reference module 100 and the solar irradiance detected by the clean reference cell 102. These quantities are analyzed, either by the measurement and control unit 104 or by a remote computing system (not shown) in order to determine the expected electrical output of the soiled reference module 100 at the given conditions of temperature and irradiance were the module to be clean, and therefrom to determine the fraction of output power from the soiled reference module 100 that is lost due to soiling, or, equivalently, the fraction of power actually generated in the soiled state compared to the power which could be generated in the clean state.

The measurement and control unit 104 is powered by AC or DC power provided, in one embodiment, through power entry conduit 120. In one embodiment, the system includes a battery for backup power; in one embodiment, the battery is located within the measurement and control unit 104. In another embodiment, the system is powered by one or more of the reference devices (100, 101, and/or 102) through a process in which the measurement and control unit 104 harvests power from the reference devices (100, 101, and/or 102) in between measurements and stores energy for use during measurements; for example, harvested energy may be stored in a battery located within measurement and control unit 104.

The measurement and control unit 104 communicates with remote computing, data logging, and/or control systems via a wired or wireless communication method. In one embodiment, communication is via an Ethernet cable, which, in one embodiment, is passed through communication conduit 122.

In one embodiment, the enclosures of the elements depicted in FIG. 5 are weather-resistant for prolonged outdoor use.

In alternative embodiments, any of the elements described may be combined within a lesser or greater number of separate enclosures than depicted in FIG. 5. In one embodiment, the clean reference cell 102 and the measurement and control unit 104 are combined into a single unit. In another embodiment, these are further combined with the wash unit 108.

Measured Electrical Output

In one embodiment, the measured electrical output parameter of the soiled reference module 100 is the short-circuit current ($I_{sc}$), from which, following temperature correction, the output maximum power ($P_{max}$) of the soiled reference module 100 is estimated using known parameters of the soiled reference module 100.

In another embodiment, the measured electrical output parameters of the soiled reference module 100 may include, in addition to the short-circuit current ($I_{sc}$), any of the maximum power ($P_{max}$), open-circuit voltage ($V_{oc}$), voltage at maximum power point, current at maximum power point, or the entire current-voltage relationship ("I-V curve"). To measure these additional parameters, the measurement and control unit 104 performs a sweep during which the I-V curve is measured and then analyzes the I-V curve. This analysis could also be performed on a remote computing system.

Any of the measured parameters may be corrected for temperature and/or irradiance, using methods known in the art and based on stored constants.

By measuring the I-V curve, the actual maximum power of the soiled reference module 100 may be directly measured, rather than estimated from the short-circuit current.

When soiling is uniformly distributed across the soiled reference module 100, estimation of the maximum power from the short-circuit current may be more accurate than direct measurement, due to the higher measurement uncertainties associated with measurement and temperature-correction of the maximum power.

However, when soiling is non-uniformly distributed, estimation of the maximum power from the short-circuit current may be very inaccurate, as discussed above.

In one embodiment, both the short-circuit current and maximum power are used to determine soiling-related power losses, and software within the measurement and control unit 104, or within a remote computing device, determines the most accurate result. For example, in one embodiment, the soiling-related power loss is determined exclusively from the measured maximum power whenever the difference between this loss and that determined exclusively from the short-circuit current exceeds the difference in uncertainty between the two measurements, or whenever the difference in uncertainty is negligible.

In one embodiment, the system uses the measurements of both short-circuit current and maximum power to report a metric which quantifies the degree of non-uniformity of the soiling. Under certain situations this metric may indicate actionable problems with the solar power plant.

In one embodiment, the measurement and control unit 104 holds the soiled reference module 100 in a designated electrical state in between measurements in order to prevent or reduce long-term degradation or other performance changes of the soiled reference module 100 that may occur in certain electrical states. The designated electrical state may include short-circuit, open-circuit, maximum power, or others. For example, crystalline silicon PV modules may be held at open-circuit in between measurements, in order to reduce degradation due to hot-spots that may occur for prolonged operation at short-circuit.

Measurement Circuit

The measurement and control unit 104 contains measurement channels for the soiled reference module 100 and either the clean reference module 101 or clean reference cell 102. In one embodiment, the measurement channel for the soiled reference module 100 measures any of its characteristic I-V parameters as described above, including short-circuit current and maximum power. In one embodiment, the measurement channel contains a sweep circuit comprising a transistor in series with the soiled reference module 100, wherein the transistor may be controlled to moderate and sweep the current flowing through the soiled reference module 100 while its current and voltage are measured by the measurement channel, thereby collecting an I-V curve. Similarly, to measure irradiance using the clean control device, in one embodiment, a sweep circuit measures the I-V curve of the clean reference module 101, or, in another embodiment, of the clean reference cell 102. In other embodiments, a sweep circuit measures only the short-circuit current of a clean reference module 101 or clean reference cell 102, without sweeping its I-V curve, by maintaining the sweep circuit in the short-circuit condition.

The I-V curve sweep time must be sufficiently short to prevent excessive heating of the sweep circuit during the I-V sweep (due to received power from the soiled reference module 100 or clean reference module 101); sufficiently short to minimize the impact of irradiance changes during the sweep; sufficiently long to allow accurate measurement of current and voltage during the sweep; and sufficiently long so that the soiled reference module 100 or clean reference module 101 capacitance does not affect the measured current and voltage data. Sweep times on the order of 100 milliseconds to 1 second would typically meet these requirements; however, other times may also be employed and remain within the scope of this disclosure.

In one embodiment, the sweep circuit may progress either from short-circuit to open-circuit or vice versa. In one embodiment, in between measurements the circuit may be held in either the short-circuit or open-circuit condition.

Figure 6:
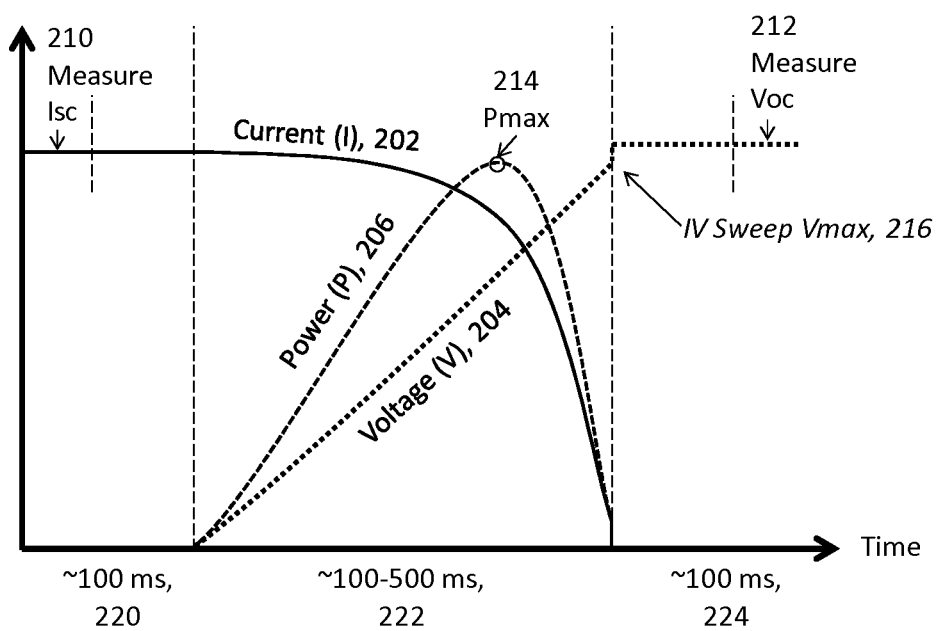
FIG. 6 depicts a transient measurement of an I-V curve in one embodiment of the measurement and control unit 104.

FIG. 6 depicts one embodiment of an I-V curve sweep and extraction of parameters from the measured I-V data. In FIG. 6, the sweep is assumed to progress from a short-circuit condition to an open-circuit condition of the soiled reference module 100. Curves 202 and 204 depict the measured current and voltage versus time during the sweep, while curve 206 depicts the power calculated from the measured current and voltage curves 202 and 204. The sweep is divided into three periods, corresponding to an initial low impedance state 220, a transition state 222, and a high impedance state 224 of the sweep circuit. During the initial low-impedance state 220, which lasts on the order of 10-100 ms following triggering of the sweep circuit, the sweep circuit maintains the module at the short-circuit condition, and, in one embodiment, the $I_{sc}$ value is measured during an initial period 210. In the transition state 222, which lasts on the order of 100-500 ms, the voltage is ramped upwards towards a maximum value indicated as 216, causing the current 202 to fall. During the final high-impedance state 224, which lasts on the order of 10-100 ms, the sweep circuit forces the soiled reference module 100 to its open-circuit condition and, in one embodiment, the $V_{oc}$ value is measured during a final time period 212. The $P_{max}$ value 214 is calculated by analysis of the calculated power curve 206, and, in one embodiment, the $I_{sc}$ and/or $V_{oc}$ values are determined by analysis of the measured current 202 versus voltage 204 curves. In one embodiment, the ramp rate of the voltage curve 204, or equivalently, the IV Sweep $V_{Max}$ value 216, are programmable and controlled by software within the measurement and control unit 104. Typically, the sweep would be set so that the voltage curve 204 reaches the soiled reference module 100 Voc value just before the onset of the high-impedance state 224, stretching the measured I-V curves to fill the transition state region 222 for optimal data acquisition quality. FIG. 6 illustrates an alternate (undesirable) condition where the voltage curve 204 does not reach all the way to the Voc value before the onset of the high-impedance state 224, whereupon the sweep circuit cuts off the soiled reference module 100 current to end the sweep. In one embodiment, the direction of the sweep could also be reversed. In one embodiment, the sweep always ends in either the high-impedance or low-impedance state, thereby minimizing power dissipation in the sweep circuit. The example is given for measurement of the soiled reference module 100, but applies equally to the clean reference module 101 or clean reference cell 102. Although specific time periods are provided for reference, other time periods could be employed and remain within the scope of this disclosure.

Figure 7:
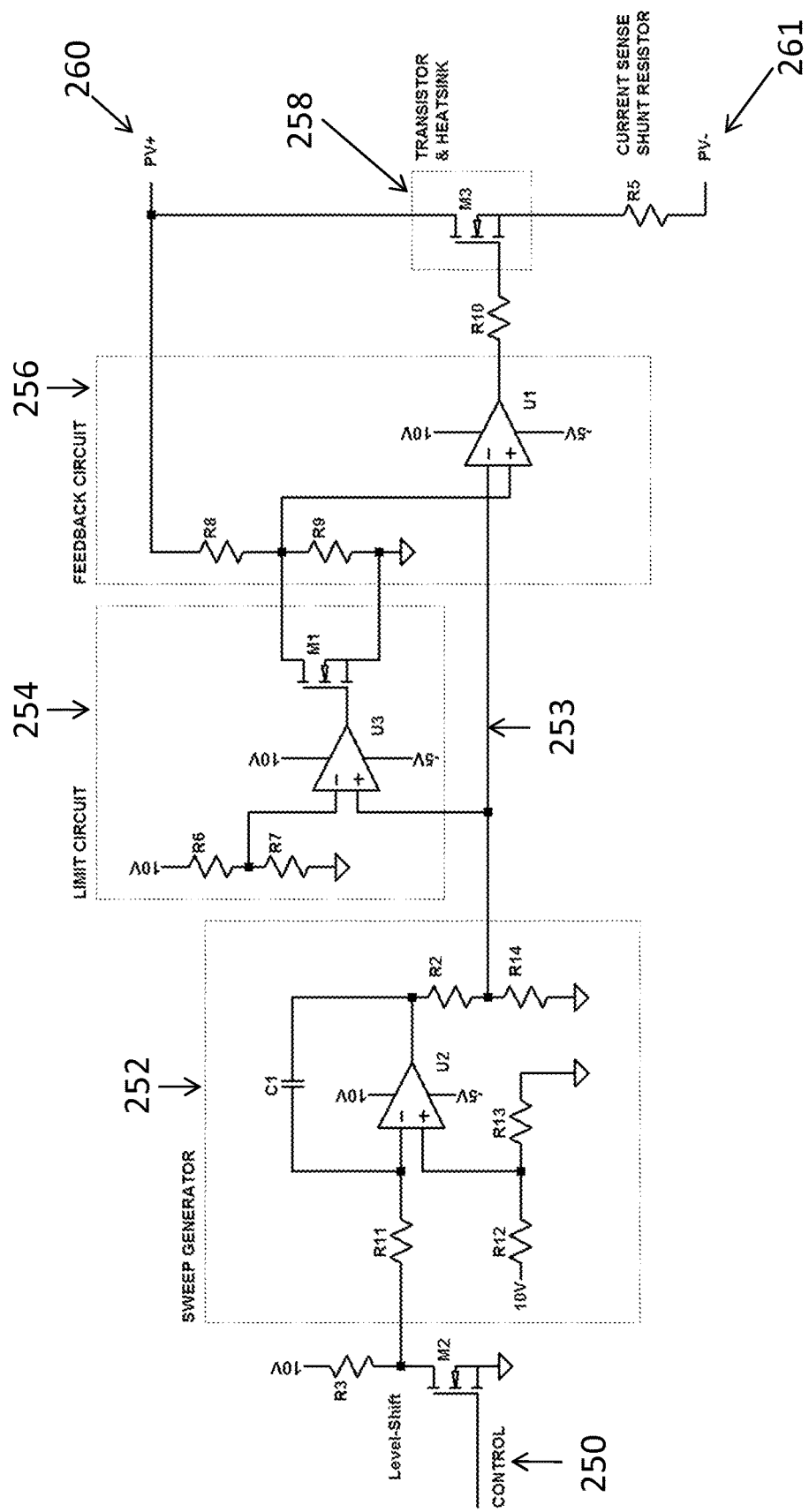
FIG. 7 depicts an embodiment of the I-V sweep circuit of the measurement and control unit 104.

FIG. 7 depicts one embodiment of an implementation of the sweep circuit. A sweep generator circuit 252 responds to a control signal 250, e.g. from a microcontroller, and produces a low-voltage ramp signal 253. The voltage of the ramp signal 253 is used to program a feedback circuit 256 which controls one or more transistor elements 258 connected in series between the input terminals 260 and 261 and a sense resistor R5 of a current measurement circuit. Initially the ramp signal 253 is saturated at one supply rail of U2, causing the sweep circuit to remain in the low-impedance state 220. Following an integration period, the sweep circuit enters the transition state 222, during which the feedback circuit 256 controls the transistor elements 958 in order to maintain the voltage at 960 equal to the low voltage ramp signal 253 times a gain factor set by R8 and R9. Finally the limit circuit 254 detects the endpoint of the low voltage ramp signal 253 and forces the sweep circuit into the high impedance state 224 by raising the gain of the feedback circuit 256. In one embodiment, the gain of the feedback circuit 256 is programmable from a microcontroller, e.g. by replacing R9 with a programmable digital potentiometer integrated circuit. In one embodiment, the sweep time can be altered by additional controls that modify the ramp rate of the sweep generator circuit 252 or bypass the ramp signal 253. In one embodiment, the sweep circuit contains additional elements (not shown) for frequency compensation and amplifier stability.

Mounting of Reference Devices

In one embodiment the mounting rack 106 is a separate mounting structure dedicated to the measuring system, as depicted in the embodiment of FIG. 5, while in another embodiment the mounting rack 106 is a part of the mounting structure for the power-producing modules of the solar power plant. In one embodiment the mounting rack 106 holds the pair of reference devices (100 and 101, or 100 and 102) in a fixed position, while in another embodiment, typically when the mounting rack 106 is part of the mounting structure for the power-producing modules of the solar power plant, it rotates about one or more axes in order to track the position of the sun throughout the day.

In order to minimize measurement errors, the pair of reference devices (100 and 101, or 100 and 102) should be held coplanar with each other preferably within less than 0.5 degrees.

In one embodiment, the system includes mechanical mounting features that ensure such alignment.

In another embodiment, the system includes adjustment mechanisms to enable the mounting angles to be calibrated. For example, in one embodiment, clean reference cell 102 is provided with one or more alignment screws 430, in alignment screw brackets 432, which press against a mounting plate 432 in order to adjust the alignment. In one embodiment, two such alignment screws are provided in order to adjust the alignment along two axes, including an azimuthal and a tilt angle.

In another embodiment, software operating within the measurement and control unit 104 or within a remote computing system corrects the measurements for the effect of angular differences.

In one embodiment, the effect of any residual angular alignment differences between the soiled reference module 100 and clean reference module 101 or clean reference cell 102 is reduced by averaging the measured readings of soiling-related power loss throughout the course of a day. For example, in the case where the pair of reference devices (100 and 101, or 100 and 102) have a slight difference in azimuthal alignment, a bias error will occur where one of the pair of reference devices (100 and 101, or 100 and 102) receives more irradiance than the other in the morning and less in the afternoon. The effect of this error may be greatly reduced by averaging equal contributions of readings from before and after the local solar noon time of each day.

Wash Unit

Figure 8:
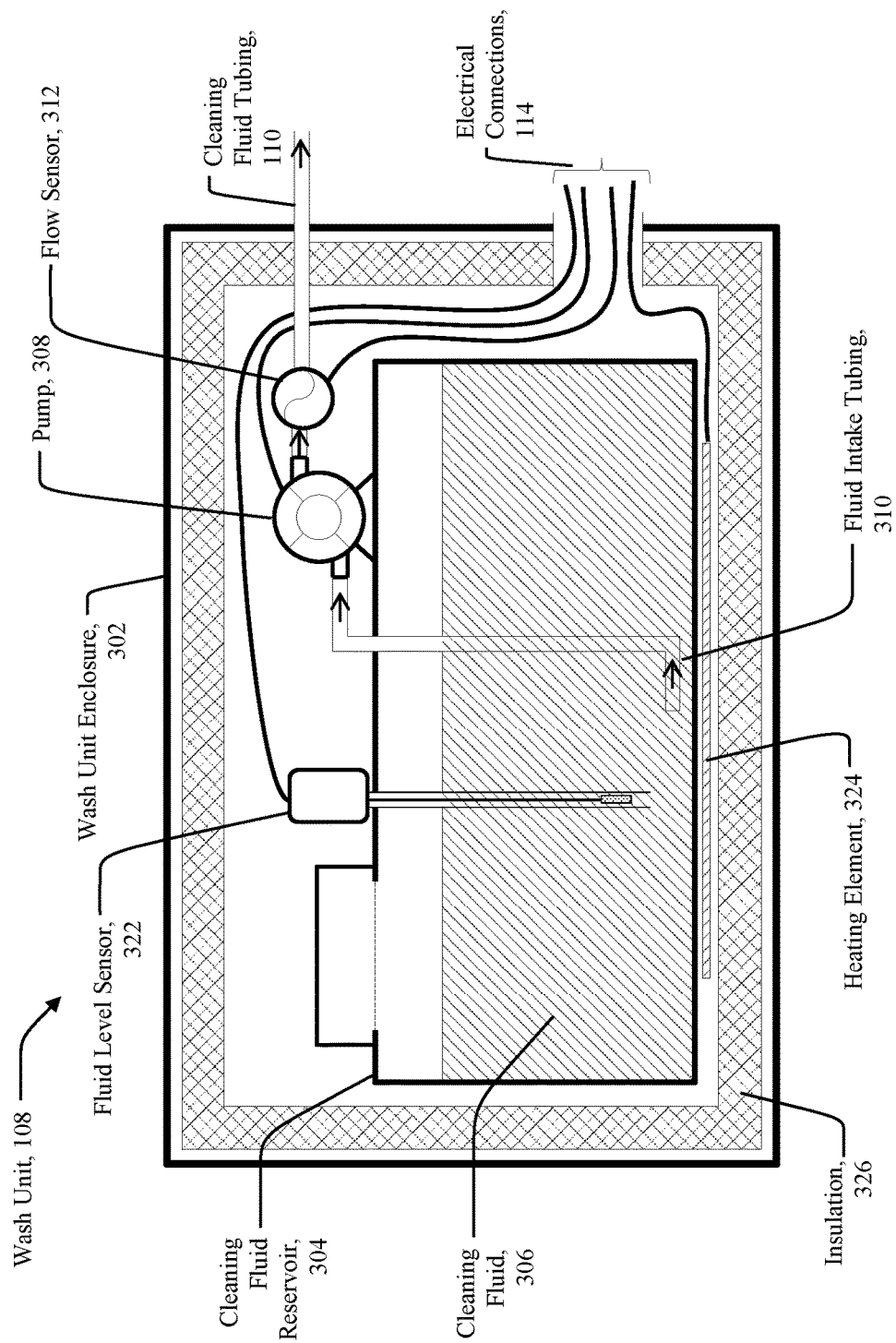
FIG. 8 depicts an embodiment of the wash unit 108.

FIG. 8 depicts an embodiment of the wash unit 108 intended to be used for automated cleaning of the clean reference cell 102.

The wash unit 108 is housed in the wash unit enclosure 302 and comprises a cleaning fluid reservoir 304, cleaning fluid 306, and pump 308 for delivering the cleaning fluid 306 from the fluid intake tubing 310 to the spray nozzle 112 via cleaning fluid tubing 110.

In one embodiment the cleaning fluid 306 is water.

In another embodiment, the cleaning fluid 306 is a solution containing anti-freeze properties allowing operation and storage in sub-freezing temperatures, for example down to −25° C. Suitable cleaning fluids, include, for example, automobile windshield washing fluids, especially those formulated to be environmentally benign.

In one embodiment, a collection tray 124 is provided underneath the clean reference cell 102 to collect cleaning fluid 306 and prevent it from spilling onto the ground and/or to recapture the cleaning fluid 306 and direct it back into the cleaning fluid reservoir 306 for re-use.

In one embodiment, the cleaning fluid reservoir 304 of the wash unit 108 contains a fluid level sensor 322 that indicates when the cleaning fluid reservoir 304 is nearly empty. The measurement and control unit 104 senses low fluid levels and reports the need for refilling the cleaning fluid reservoir 304.

In one embodiment, the wash unit 108 includes a flow sensor 312 for measuring the flow rate of cleaning fluid 306 during operation of the wash unit 108. The flow rate is sensed by the measurement and control unit 104 in order to determine whether flow is within acceptable limits and thereby identify faults with the system. In another embodiment, a flow sensor 313 is located near the discharge point of the fluid into the spray nozzle 112, within the enclosure housing the clean reference cell 102, thus providing the additional ability to identify any leaks or blockages between the wash unit 108 and the clean reference cell 102.

In one embodiment, the flow rate is measured in order to determine the volume of cleaning fluid 306 dispensed and to operate the wash unit 108 until a predetermined fluid volume has been dispensed, ensuring repeatable cleaning and minimal use of cleaning fluid 306. This may particularly be required in situations where height difference between the clean reference cell 102 and the wash unit 108 is variable (e.g. when the reference devices 100,102 are mounted on a tracking system), leading to variable pressure within the cleaning fluid tubing 110.

In one embodiment, the temperature of the clean reference cell 102 is measured during operation of the wash unit 108 in order to determine whether the cleaning system is operating correctly. Under sunny conditions, application of cleaning fluid 306 to the clean reference cell 102 should result in a momentary decrease in temperature. The measurement and control unit 104 detects whether the temperature of the clean reference cell 102 decreases in the expected manner, thus allowing potential identification of faults such as leaks, blockages, or mis-direction of the spray nozzle 112.

In one embodiment, the wash unit 108 is provided with insulation 326 and/or with at least one heating element 324 to prevent freezing of the cleaning fluid 306 in cold conditions. The heating element 324 may be controlled by measurement and control unit 104.

Reference Cell

Figure 9:
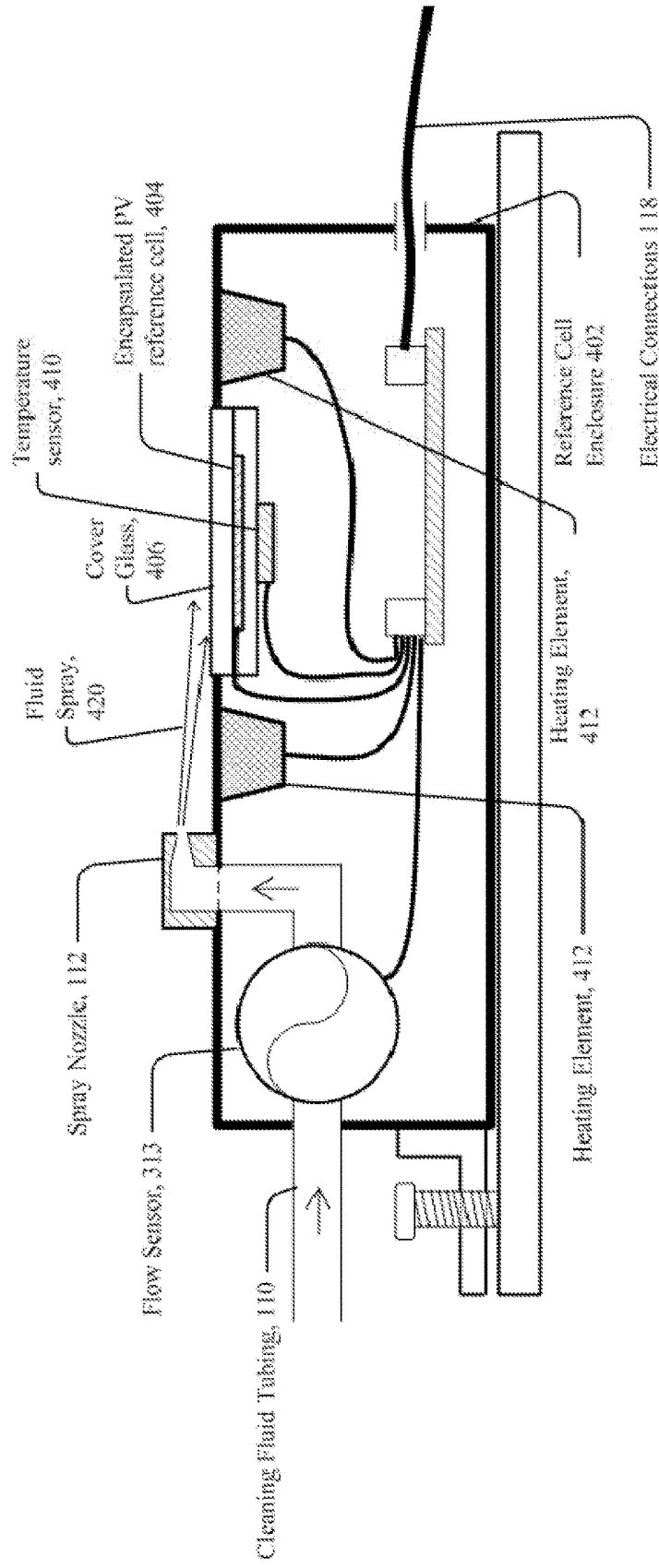
FIG. 9 depicts an embodiment of the clean reference cell 102.

FIG. 9 depicts one embodiment of the clean reference cell 102 that has special features for use within a system of the disclosed subject matter, beyond those of a PV reference cell of typical construction.

The clean reference cell 102 is housed in reference cell enclosure 402. An encapsulated PV reference cell 404, comprising a cell of photovoltaic material bonded within an encapsulant material and further bonded to a cover glass 406, in one embodiment, is mounted within the reference cell enclosure 402. The mounting mechanism provides a temporary or permanent seal which prevents moisture entry to the reference cell enclosure 402. In one embodiment, a temperature sensor 410, such as a resistive temperature detector, is fixed in thermal contact with the back side of the encapsulated PV reference cell 404.

In one embodiment an optical filter is integrated within the reference cell enclosure 402 or used in place of cover glass 406, in order to adjust the spectral response of the encapsulated PV reference cell 404 to provide better spectral response matching with soiled reference module 100.

A spray nozzle 112 directs cleaning fluid 306 from cleaning fluid tubing 110 onto the cover glass 406 of the encapsulated PV reference cell 404, providing fluid spray 420 which cleans the cover glass 406.

In one embodiment, spray nozzle 112 is mounted on reference cell enclosure 402 and cleaning fluid tubing 110 passes cleaning fluid 306 through the reference cell enclosure 402. In another embodiment, the mounting of spray nozzle 112 is not integral to reference cell enclosure 402 but comprises, for example, a separate bracket which holds spray nozzle 112 near reference cell enclosure 402, such that cleaning fluid tubing 110 need not be connected to reference cell enclosure 402.

In one embodiment, a flow sensor 313 included within or near the reference cell enclosure 402 measures the flow rate of cleaning fluid 306 to the spray nozzle 112. The flow rate is measured in order that the system may dispense a minimally sufficient quantity of cleaning fluid 306 and/or to ensure proper operation of the system and absence of leaks, as discussed above.

In one embodiment, reference cell enclosure 402 contains one or more heating elements 412 which heat the reference cell enclosure 402. In one embodiment, heating elements 412 are mounted to the inside top side of the reference cell enclosure 402, to preferentially heat the top side.

In one embodiment, reference cell enclosure 402 contains a circuit board 416 through which connections to each of the enclosed electrical elements are provided, as depicted in FIG. 5.

In one embodiment, the clean reference cell 102 is provided with one or more alignment screws 430, in alignment screw brackets 432, which press against a mounting plate 432 in order to adjust the alignment. In one embodiment, two such alignment screws 432 are provided in order to adjust the alignment along two axes, including an azimuthal and a tilt angle.

Measurement of Snow Losses

The accumulation of snow, ice, and frost on modules within a solar power plant produces power losses in a manner similar to that associated with the accumulation of soiling, by preventing solar irradiance from reaching all or portions of the modules. Such snow-related (including ice- and frost-related) power losses may also be measured by the system of the disclosed subject matter, provided that the clean reference cell 102 is kept free of accumulated snow, ice, and frost in order that it may accurately measure the incident solar irradiance.

In one embodiment, the reference cell enclosure 402 is heated by heating elements 412 to melt snow, ice, and/or frost accumulated on top of the reference cell enclosure 402, causing the snow, ice, and/or frost to evaporate and/or slide off. In one embodiment, heating elements 412 are activated based on readings of the temperature of the clean reference cell 102 measured with temperature sensor 410. In another embodiment, heating elements 412 are activated based on externally or remotely meteorological data that indicate the likely presence of snow, ice, or frost.

In one embodiment, the wash unit 108 is used to partially or completely remove accumulated snow, ice, or frost from the clean reference cell 102. In one embodiment, this is done by spraying cleaning fluid 306 with anti-freeze properties on the clean reference cell 102. In one embodiment, the cleaning fluid 306 may be heated.

In one embodiment, a gap (not depicted in FIG. 5) is provided surrounding the clean reference cell 102, such that any snow sliding off of adjacent surfaces (e.g. the soiled reference module 100) does not slide onto the clean reference cell 102.

Calibration

Accurate determination of soiling-related power losses by comparison of the outputs of the reference devices (100 and 101 or 100 and 102) may require that both the reference devices (100 and 101 or 100 and 102) and the measurement and control unit 104 be calibrated.

In one embodiment, both the clean reference cell 102 and the measurement and control unit 104 are calibrated in a laboratory or manufacturing environment prior to delivery to the installation site and subsequently recalibrated as needed or at periodic intervals either in a laboratory or at the installation site.

In one embodiment, the soiled reference module 100 and/or clean reference module 101 are also calibrated in a laboratory environment prior to delivery to the installation site.

However, laboratory calibration results in significant expenses related to removing modules from service, shipping them to and from calibration laboratories, and re-installing them into service. Therefore, in another embodiment, the soiled reference module 100 and/or clean reference module 101 are calibrated and/or recalibrated at the installation site using portable equipment. In another embodiment, the soiled reference module 100 and/or clean reference module 101 are automatically calibrated by the system of the disclosed subject matter. In this embodiment, when both the soiled reference module 100 and the clean reference module 101 or clean reference cell 102 are known to be in a clean state, e.g. after cleaning by personnel or after rain events, measurements performed by the measurement and control unit 104 are used to determine either relative or absolute calibration constants, with analysis being performed either within the measurement and control unit 104 or within a remote computing device.

Data Analysis

In one embodiment, measured data are analyzed to filter out measurements performed during periods of rapidly changing irradiance, e.g. due to passing clouds affecting the clean reference cell 102 and soiled reference module 100 differently at an instant in time.

In one embodiment, measured data are integrated or averaged over portions of the day including approximately equal contributions of measurements both before and after solar noon, in order to minimize errors associated with angular alignment differences between the reference devices (100 and 101 or 100 and 102).

In one embodiment, measured data are analyzed to determine rates of change over time of soiling-related losses, in addition to or instead of determining soiling-related power losses.

Multiple Devices

In one embodiment, the system contains multiple soiled reference modules 100, and a soiling-related power loss is determined for each.

In one embodiment, the system contains multiple clean reference modules 101 or clean reference cells 102.

In one embodiment, multiple measurement and control units 104 are networked together, the entire system thereby measuring multiple reference devices (100, 101, and/or 102).

Irradiance Measurement

In one embodiment, the system is used for the purpose of irradiance measurement, in addition to or instead of for the purpose of measuring soiling-related power losses, and the soiled reference module 100 may be omitted. In one embodiment, the system comprises an irradiance sensor, which may comprise either a clean reference cell 102 or a pyranometer which can take the place of the clean reference cell 102. The irradiance sensor is cleaned with the automatic cleaning unit Although example diagrams to implement the elements of the disclosed subject matter have been provided, one skilled in the art, using this disclosure, could develop additional hardware and/or software to practice the disclosed subject matter and each is intended to be included herein.

In addition to the above described embodiments, those skilled in the art will appreciate that this disclosure has application in a variety of arts and situations and this disclosure is intended to include the same.

While the invention has been described with respect to a limited number of embodiments, the specific features of one embodiment should not be attributed to other embodiments of the invention. No single embodiment is representative of all aspects of the inventions. Moreover, variations and modifications there from exist. For example, the invention described herein may comprise other components. Various additives may also be used to further enhance one or more properties. In some embodiments, the inventions are substantially free of any additive not specifically enumerated herein. Some embodiments of the invention described herein consist of or consist essentially of the enumerated components. In addition, some embodiments of the methods described herein consist of or consist essentially of the enumerated steps. The appended claims intend to cover all such variations and modifications as falling within the scope of the invention.

What is claimed is:

1. A system for measuring electrical output loss in a photovoltaic array due to soiling, comprising:
   a pair of photovoltaic reference devices placed substantially proximate to the photovoltaic array and substantially co-planar to modules forming the array, said pair of photovoltaic reference devices comprising:
      a first reference device, designated as a soiled reference device, comprising a photovoltaic module representative of a portion of the photovoltaic array, wherein the soiled reference device is allowed to accumulate soiling at a rate representative of the rate of soiling of the photovoltaic array;
      a second reference device, designated as a clean reference device, comprising a photovoltaic module or cell, wherein a sensing surface of said clean reference device is maintained substantially clean and free of accumulated soiling;
   a measurement unit for performing measurements of a subpart, wherein said subpart comprises said soiled reference device, said clean reference device, and combination thereof;
      wherein said measurements of the soiled reference device comprise measurements of a short-circuit current, a maximum power output, and combinations thereof; and
      wherein said measurements of said clean reference device comprise measurements of said short-circuit current; and
   a computing device, wherein said computing device analyzes said measurements associated with said subparts for determining a soiling impact analysis.

2. The system of claim 1, wherein said measurement unit further comprises a temperature sensor for measuring a temperature of said subpart, wherein said measurement comprises a measurement from a group consisting essentially of temperature of said subpart, a temperature difference across said subpart, and combinations thereof.

3. The system of claim 1, wherein said measurement unit comprises a sensor for producing subparts measurements from a group consisting essentially of said short-circuit current, said maximum power output, an open-circuit voltage, and combination thereof.

4. The system of claim 3, wherein said measurement unit maintains said subpart in a designated electrical state between performance of said measurements, wherein the designated electrical state comprises an electrical state from a group consisting essentially of a short-circuit state, an open-circuit state, and a maximum power state.

5. The system of claim 3, said measurement unit further comprising a sweep circuit that measures a current-voltage relationship of said subpart, wherein said current-voltage relationship comprises measurements through the range of said short-circuit current, said maximum power output, and an open-circuit voltage.

6. The system of claim 5, wherein said sweep circuit comprises a transistor positioned in series with said subpart, and further wherein said transistor modulates the current of said subpart, and wherein said sweep circuit progresses through a transition, said transition consisting essentially of from a low-impedance state to a high-impedance state, and/or from a high-impedance state to a low-impedance state,
   wherein said measurement of said current-voltage relationship occurs during said transition; and
   further wherein said sweep circuit additionally comprises a limit circuit for instructing said sweep circuit from a first to a second impedance state within a predetermined time.

7. The system of claim 1, wherein said measurement unit compares soiling-induced losses determined from said short-circuit current and said maximum power output of said soiled reference device for quantifying a degree of non-uniformity of soiling on said soiled reference device.

8. The system of claim 1, wherein said computing device stores a difference in angular alignment of said subpart and the photovoltaic array, or a difference in angular alignment of the pair of reference devices, and wherein said computing device corrects said measurements for the differences in angular alignment.

9. The system of claim 1, wherein said computing device stores a difference in angular alignment between said subparts or between said subparts and the photovoltaic array, and wherein a computing device corrects the measurements for the differences in angular alignment.

10. The system of claim 1, wherein an effect of differences in angular alignment between the pair of reference devices or between said subpart and the photovoltaic array is minimized by averaging measurements including substantially equal contributions of measurements before and after the time of local solar noon of each day.

11. The system of claim 1, wherein said subpart supplies power to said measurement unit between performances of said measurements.

12. The system of claim 1, wherein said computing device utilizes said measurements of said clean reference device to calibrate said measurements of said soiled reference device during a period in which said soiled reference device is known to be substantially clean.

13. The system of claim 1, wherein said system further comprises an automatic cleaning unit, wherein said automatic cleaning unit maintains a soiling free surface of said clean reference device.

14. The system of claim 13, wherein said automatic cleaning unit uses a pressurized gas stream directed at said clean reference device to remove accumulated soiling.

15. The system of claim 13, wherein said automatic cleaning unit comprises a cleaning fluid reservoir and a pump for directing said cleaning fluid through a spray nozzle onto a cover surface of said clean reference device for removing accumulated soiling.

16. The system of claim 15, additionally comprising a collection tray which captures dispensed cleaning fluid to prevent spilling and/or for re-use in said cleaning fluid reservoir.

17. The system of claim 15, wherein said cleaning fluid resists freezing.

18. The system of claim 15, wherein said automatic cleaning unit further comprises insulation, a heater, or combination thereof, for preventing freezing of said cleaning fluid.

19. The system of claim 15, wherein a housing of said clean reference device incorporates said spray nozzle.

20. The system of claim 15, additionally comprising a flow sensor for measuring a flow rate of said cleaning fluid, wherein dispensing of said cleaning fluid continues until either an integrated measured flow reaches a predetermined limit, or a measured flow rate signals a fault condition.

21. The system of claim 20, wherein said flow sensor is positioned immediately adjacent to said spray nozzle, whereby said system is capable of determining a presence of a leak between said cleaning fluid reservoir and said spray nozzle.

22. The system of claim 15, wherein said system is capable of determining that said cleaning fluid properly reaches said clean reference device according to a temperature measurement of said clean reference device, a measured temperature change of said clean reference device, and combination thereof.

23. The system of claim 1, further comprising a heater for removing an accumulation of frozen precipitation from a surface of said clean reference device, and wherein according to said measurements of said clean reference device, said system determines an electrical output loss value for the soiled reference device resulting from said frozen precipitation.

24. The system of claim 23, wherein an enclosure of said clean reference device incorporates said heater.

25. An apparatus for measuring solar irradiance, comprising:
an irradiance sensor, said irradiance sensor comprising:
a photovoltaic reference device or a pyranometer; and
an automatic cleaning unit capable of cleaning a surface of said irradiance sensor to remove accumulated soiling,
wherein the automatic cleaning unit comprises a cleaning fluid reservoir and a pump to direct a cleaning fluid onto said surface of said irradiance sensor through a spray nozzle; and
a heater capable of removing an accumulation of frozen precipitation from said apparatus;
a temperature sensor for measuring a temperature of said irradiance sensor, and wherein from measuring a temperature of said irradiance sensor the apparatus is capable of confirming that said cleaning fluid properly reaches said irradiance sensor.

26. The apparatus of claim 25, additionally comprising a flow sensor for measuring a flow rate of said cleaning fluid, wherein dispensing of said cleaning fluid continues until either an integrated measured flow reaches a predetermined limit, or a measured flow rate signals a fault condition.

27. A method for measuring electrical output loss value in a photovoltaic array due to soiling, comprising:
measuring by a first sensor from a soiled reference device a first short-circuit current and a maximum power output;
measuring by a second sensor from a clean reference device a second short-circuit current;
determining a clean state associated with said clean reference device; and
analyzing said measurements by a computing device to determine a soiling impact analysis.

* * * * *